US006469109B2

(12) United States Patent
Ueda et al.

(10) Patent No.: US 6,469,109 B2
(45) Date of Patent: Oct. 22, 2002

(54) ARYL ESTER COMPOUND, ITS PRODUCTION PROCESS, EPOXY RESIN COMPOSITION USING SAID COMPOUND, AND COPPER-CLAD LAMINATE USING THE EPOXY RESIN COMPOSITION

(75) Inventors: Youichi Ueda, Takatsuki (JP); Yasuhiro Endo, Tsukuba (JP); Mitsuhiro Shibata, Ibaraki-ken (JP); Kaori Yamasaki, Ibaraki (JP)

(73) Assignee: Sumitomo Chemical Company, Limited, Osaka (JP)

(*) Notice: Subject to any disclaimer, the term of this patent is extended or adjusted under 35 U.S.C. 154(b) by 0 days.

(21) Appl. No.: 08/885,191

(22) Filed: Jun. 30, 1997

(65) Prior Publication Data

US 2002/0010288 A1 Jan. 24, 2002

Related U.S. Application Data

(62) Division of application No. 08/520,110, filed on Aug. 28, 1995, now Pat. No. 5,726,257.

(30) Foreign Application Priority Data

| Aug. 30, 1994 | (JP) | ............................................. 6-205175 |
| Sep. 27, 1994 | (JP) | ............................................. 6-231182 |
| Jan. 30, 1995 | (JP) | ............................................. 7-012437 |
| Feb. 2, 1995  | (JP) | ............................................. 7-016183 |

(51) Int. Cl.$^7$ ............................ C08G 8/02; C08G 8/04; C08G 8/22
(52) U.S. Cl. ..................... 525/507; 525/508; 528/87; 528/88; 528/102; 528/128; 528/155; 528/161
(58) Field of Search ................................. 525/507, 508; 528/87, 88, 102, 128, 155, 161

(56) References Cited

U.S. PATENT DOCUMENTS

| 3,861,921 A | * | 1/1975 | Hoffmann et al. .......... 156/330 |
| 4,786,579 A | * | 11/1988 | Tazawa et al. .............. 430/280 |
| 5,283,324 A | | 2/1994 | Tomioka et al. |
| 5,290,657 A | | 3/1994 | Uetani et al. |
| 5,344,899 A | * | 9/1994 | Enomoto et al. ........... 525/534 |
| 5,374,742 A | | 12/1994 | Uetani et al. |
| 5,436,107 A | | 7/1995 | Tomioka et al. |
| 5,556,995 A | | 9/1996 | Suzuki et al. |
| 5,587,492 A | | 12/1996 | Tomioka et al. |
| 5,872,196 A | * | 2/1999 | Murata et al. .............. 525/508 |

FOREIGN PATENT DOCUMENTS

| EP | 0 021 827 A1 | 1/1981 |
| EP | 0 458 988 A1 | 12/1991 |
| EP | 0 496 698 A2 | 7/1992 |
| EP | 0 505 987 A1 | 9/1992 |
| EP | 0 509 431 A1 | 10/1992 |
| EP | 0 089 387 A1 | 9/1993 |
| EP | 0 582 309 A2 | 2/1994 |
| EP | 0 590 463 A2 | 4/1994 |
| EP | 0 598 320 A2 | 4/1994 |
| JP | 62053327 | * 3/1987 |
| WO | WO 95/20612 | 8/1995 |

OTHER PUBLICATIONS

Patent Abstracts of Japan, vol. 17, No. 611 (P–1641), Nov. 10, 1993 & JP 05 188590.
Patent Abstracts of Japan, vol. 17, No. 327 (C–1073), Jun. 22, 1993 & JP 05 032654A.
Patent Abstracts of Japan, vol. 18, No. 558 (C–1264), Oct. 25, 1994 & JP 06 199989A.
Patent Abstracts of Japan, vol. 18, No. 383 (C–1640), Jul. 19, 1994 & JP 06 106676A.
Patent Abstracts of Japan, vol. 18, No. 383 (C–1640), Jul. 19, 1994 & JP 06 106674A.
Chemcial Abstracts, vol. 105, No. 5, (Aug. 4, 1986), F. Matsunaga et al., "Oxyflavans", p. 712, No. 42541u, JP 61–27 980 A.
Chemical Abstracts, vol. 119, No. 24 (Dec. 13, 1993), K. Hashimoto et al., "Manufacture of Novolak Resin and Positive–working Photoresist Composition", p. 726, No. 259 599e.
Chemical Abstracts, vol. 121, No. 18 (Oct. 31, 1994), T. Morimoto et al., "Epoxy Resins and Their Compositions for Potting and Electronic Device Packaging", p. 105, No. 207 371j.

* cited by examiner

*Primary Examiner*—Jeffrey Mullis
(74) *Attorney, Agent, or Firm*—Fitch, Even, Tabin & Flannery

(57) ABSTRACT

An epoxy resin composition is disclosed as containing, as essential components, an epoxy resin, an aryl ester compound obtained from a polyhydric phenol representedd by a formula (4) with a carbonyl compound represented by a general formula (2) and a cure accelerator. When cured, the resulting product has low dielectric constant and a low dielectric loss tangent. A copper-clad laminate formed using the described composition has a low dielectric constant and a low dielectric loss tangent. The copper-clad laminate exhibits excellent adhesiveness characteristics and is suitable for use in multilayer printed wiring boards in high speed operations, particularly in the high frequency region.

15 Claims, No Drawings

ARYL ESTER COMPOUND, ITS PRODUCTION PROCESS, EPOXY RESIN COMPOSITION USING SAID COMPOUND, AND COPPER-CLAD LAMINATE USING THE EPOXY RESIN COMPOSITION

This is a division of application Ser. No. 08/520,110, filed Aug. 28, 1995 now U.S. Pat. No. 5,726,257.

BACKGROUND OF THE INVENTION

1. Field of the Invention

This invention relates to an aryl ester compound which can be used mainly as a curing agent for an epoxy resin and can give a cured product having a low dielectric constant and a low dielectric loss tangent; an epoxy resin composition using the same, and a laminate prepared using the epoxy resin composition. These are suitable for a molding material, a paint and varnish, a coating material, a civil engineering material, a constructional material and in particular, in the electric or electronic uses which work at high-frequency region, for example, a resin for laminate or an IC-sealing resin.

2. Description of the Prior Art

Among the epoxy resins used in the electric and electronic uses, the resin for a printed wiring board has heretofore been mainly a combination of a bisphenol type epoxy resin with a dicyandiamide. In recent years, the resin has been required to have a low dielectric constant for the purpose of the improvement of signal velocity and the impedance-matching of circuit as the printed wiring board has been made thinner and more multiple in layer and also required to have a low dielectric loss tangent for the purpose of diminishing the signal transmission loss as a high-frequency signal is used. For these purposes, a method of combining a conventional epoxy resin with a thermoplastic resin having a low dielectric constant and a low dielectric loss tangent has been devised. For example, a method of modifying the epoxy resin with a reactive polybutadiene resin and a method of dispersing a polytetrafluoroethylene resin powder have been proposed.

However, in these prior techniques, the epoxy resin which is the basic material has a high dielectric constant, and hence, the proportion of the thermoplastic resin to be combined becomes large in order to achieve the desired dielectric constant, and hence, the heat resistance, adhesiveness, dimension stability, chemical resistance and the like which are characteristic features of the epoxy resin are damaged. Therefore, there have been earnestly desired such an epoxy resin curing agent that a cured product having a low dielectric constant and a low dielectric loss tangent can be obtained without damaging the heat resistance, adhesiveness and processibility of an epoxy resin and an epoxy resin composition containing the curing agent.

The present inventors have made extensive research on the functional group structure and skeletal structure of a compound capable of thermal cure reaction with an epoxy resin, and have consequently found that an epoxy resin composition comprising a compound having a specific functional group structure and a specific skeletal structure can meet the above-mentioned purposes.

SUMMARY OF THE INVENTION

According to this invention, there are provided an aryl ester compound composed of a polyhydric phenol in which at least one OH group has been esterified with an organic acid or its derivatives having 1 to 20 carbon atoms, said polyhydric phenol being the condensation product of a substituted or unsubstituted resorcinol represented by the general formula (1):

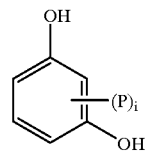

(1)

wherein each P represents independently a hydrogen atom, a halogen atom, an alkyl group having 1 to 10 carbon atoms, a cycloalkyl group having 5 to 10 carbon atoms, an aryl group having 6 to 20 carbon atoms or an aralkyl group having 7 to 20 carbon atoms and i represents an integer of 0 to 2, with a carbonyl compound represented by the general formula (2):

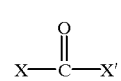

(2)

wherein each of X and X' represents independently a hydrogen atom, an alkyl group having 1 to 10 carbon atoms, a cycloalkyl group having 5 to 10 carbon atoms, an aryl group having 6 to 20 carbon atoms or an aralkyl group having 7 to 20 carbon atoms, provided that X and X' may form a ring together with the carbon atom to which X and X' are attached;

a process for producing said aryl ester compound which comprises condensing the substituted or unsubstituted resorcinol represented by the general formula (1) with the carbonyl compound represented by the general formula (2) in the presence of an acid catalyst and then esterified the condensation product thus obtained with an organic acid or its derivatives having 1 to 20 carbon atoms in the presence of a basic compound; an epoxy resin composition which comprises as the essential components:

(A) an epoxy resin, (B) an aryl ester compound composed of a polyhydric phenol in which at least one OH group has been esterified with an organic acid or its derivatives having 1 to 20 carbon atoms, said polyhydric phenol being a condensation product of a phenolic compound represented by the general formula (4):

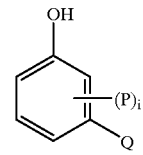

(4)

wherein P and i are the same as defined above and Q represents a hydrogen atom or a hydroxyl group, with the carbonyl compound represented by the general formula (2), and (C) a cure accelerator; and a copper-clad laminate obtained by thermoforming a copper foil and a prepreg obtained by impregnating a substrate with the above epoxy resin composition or a solution of the above epoxy resin composition in an organic solvent.

DETAILED DESCRIPTION OF THE INVENTION

The aryl ester compound of this invention and the component (B) of the epoxy resin composition of this invention are preferably aryl ester compounds represented by the general formula (3):

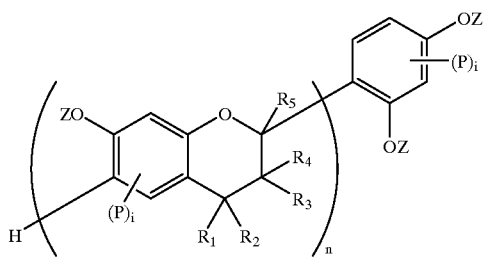

wherein n represents the average number of the repeated units and is a value of 1 to 20; each P represents independently a hydrogen atom, a halogen atom, an alkyl group having 1 to 10 carbon atoms, a cycloalkyl group having 5 to 10 carbon atoms, an aryl group having 6 to 20 carbon atoms or an aralkyl group having 7 to 20 carbon atoms; i represents an integer of 0 to 2; each of $R_1$, $R_2$, $R_3$, $R_4$ and $R_5$ represents independently a hydrogen atom, an alkyl group having 1 to 10 carbon atoms, a cycloalkyl group having 5 to 10 carbon atoms, an aryl group having 6 to 20 carbon atoms or an aralkyl group having 7 to 20 carbon atoms, provided that $R_1$ and $R_2$ may form a ring together with the carbon atom to which $R_1$ and $R_2$ are attached or $R_4$ and $R_5$ may form a ring together with the carbon atoms to which $R_4$ and $R_5$ are attached; each Z represents independently a hydrogen atom or an acyl group having 1 to 20 carbon atoms, provided that the case where all Z groups are hydrogen atoms is excluded.

In the general formula (3), Z's may be acyl groups in (n+2) places on average per one molecule (in this case, the esterification percentage is taken as 100%); however, Z's are such that the esterification percentage may be any value in other cases than where all Z groups are hydrogen atoms (in this case, the esterification percentage is 0%). In order to achieve the purpose of low dielectric constant and low dielectric loss tangent, the esterification percentage is preferably at least 30%, more preferably at least 50%.

In the general formula (3), n represents the average number of the repeated units and may be a value of 1 to 20. However, in view of operability, the average number is preferably a value of 1 to 10.

The polyhydric phenol compound which is used as the starting material for the aryl ester compound can be obtained in such a known manner that resorcinols are condensed with a carbonyl compound in the presence of an acid. The resorcinols are substituted or unsubstituted resorcinols represented by the above general formula (1).

Here, the resorcinols are such as not to have substituents at the 4- and 6-positions and includes resorcinol; alkyl resorcinols, representatives of which are 2-methylresorcinol, 5-methylresorcinol, 2-propylresorcinol, 2-n-butylresorcinol, 5-isobutylresorcinol, 5-t-butylresorcinol, 5-octylresorcinol, 5-nonylresorcinol, 2,5-dimethylresorcinol, 2,5-diethylresorcinol, 2,5-diisopropylresorcinol, 2-methyl-5-butylresorcinol, 2-methyl-5-nonylresorcinol and the like; cycloalkylresorcinols, representatives of which are 2-cyclopentylresorcinol, 2-cyclohexylresorcinol, 2-cycloheptylresorcinol and the like; arylresorcinols such as 5-phenylresorcinol, 5-naphthylresorcinol and the like; aralkylresorcinols such as 5-benzylresorcinol, 5-phenethylresorcinol and the like; and halogenated resorcinols such as 2-chlororesorcinol, 5-chlororesorcinol, 2,5-dichlororesorcinol, 2-bromoresorcinol, 5-bromoresorcinol, 2,5-dibromoresorcinol, 2-iodoresorcinol, 5-iodoresorcinol, 2,5-diiodoresorcinol and the like.

The carbonyl compound is represented by the above general formula (2). The carbonyl compound includes aldehydes, representatives of which are formaldehyde, acetaldehyde, propionaldehyde, butyraldehyde, pentylaldehyde, phenylacetaldehyde, cyclohexylacetaldehyde and the like; and ketones such as acetone, methyl ethyl ketone, diethyl ketone, methyl propyl ketone, methyl isobutyl ketone, cyclohexanone, methylcyclohexanone, cycloheptanone, benzyl phenyl ketone, benzyl methyl ketone, methyl phenethyl ketone, acetophenone, acetonaphthenone, indan-1-one and the like.

The acid catalyst used in the condensation reaction between the resorcinol and the carbonyl compound includes inorganic acids such as hydrochloric acid, sulfuric acid and the like; organic acids such as p-toluenesulfonic acid, benzenesulfonic acid, methanesulfonic acid and the like; solid acids such as acid clay, activated alumina, zeolite and the like; acidic ion exchange resins; and the like. The amount of the acid catalyst is preferably 0.01 to 50% by weight, more preferably 0.5 to 20% by weight, based on the total weight of the resorcinols and carbonyl compound charged as the starting materials.

In the condensation reaction, a known non-reactive organic solvent may be used, and this non-reactive organic solvent includes toluene, xylene, dioxane, tetrahydrofuran, N,N-dimethylformamide, N,N-dimethylacetamide and the like though these solvents are not critical.

The mole ratio of the resorcinols to the carbonyl compound in the condensation reaction is preferably 0.1:1 to 2.0:1, more preferably 0.3:1 to 1.5:1. When the ratio is outside this range, such a problem is caused that an excess of resorcinol remains or the amount of the remaining OH groups of the product becomes small. The reaction temperature is preferably 0 to 200° C., more preferably 20 to 160° C. When the temperature is lower than this range, the conversion of condensation reaction becomes low and when the temperature is higher than the range, by-products are yielded in a large amount. The reaction time is preferably 1 to 100 hours, more preferably 2 to 80 hours. When the reaction time is shorter than this range, the reaction becomes incomplete, and even if the reaction is effected for a period longer than this range, the yield is not increased, so that such a long term reaction is not economical.

In the condensation reaction, the water formed by the reaction may or may not be removed from the system. When the water is to be removed, it is sufficient to conduct the reaction using an azeotropically dehydratable solvent such as toluene, xylene or the like and a means such as a Dean-Stark tube capable of allowing the reaction to proceed while removing water from the system or the like. Moreover, in order to accelerate the dehydration, the reaction may be conducted under reduced pressure.

The esterification of the polyhydric phenol compound which is the condensation product is effected by reaction with an organic acid or its derivatives having 1 to 20 carbon atoms in the presence of a basic compound.

The organic acid and its derivatives include aliphatic monocarboxylic acids such as formic acid, acetic acid, propionic acid, butyric acid, valeric acid, lauric acid, stearic acid, phenylacetic acid, bromoacetic acid and the like; acid halides and anhydrides of the aliphatic monocarboxylic acids; aromatic monocarboxylic acids such as benzoic acid, methylbenzoic acid, naphthoic acid, biphenylcarboxylic acid and the like; acid halides and anhydrides of the aromatic monocarboxylic acids; alicyclic monocarboxylic acids such as cyclopentanecarboxylic acid, cyclohexanecarboxylic acid, cycloheptanecarboxylic acid and the like; acid halides and anhydrides of the alicyclic monocarboxylic acids; and the like. However, these are not critical.

The basic compound used in the esterification reaction includes inorganic basic compounds such as sodium hydroxide, potassium hydroxide and the like; organic basic compounds such as pyridine, triethylamine, triphenylphosphine, imidazole compounds and the like; etc.

In the esterification reaction, a known organic solvent may be used and examples thereof include toluene, xylene, acetone, methyl ethyl ketone, methyl isobutyl ketone, cyclohexanone, dioxane, tetrahydrofuran, N,N-dimethylformamide, N,N-dimethylacetamide and the like. Toluene, xylene and methyl isobutyl ketone are preferred.

In the esterification reaction, the mole equivalent ratio of the organic acid or the acid halide or anhydride thereof to the OH group of the starting polyhydric phenol compound is preferably 0.3:1 to 2.0:1, more preferably 0.5:1 to 1.5:1. When the mole equivalent ratio is outside this range, such problems are caused that an excess of an organic acid remains and the esterification percentage of the product becomes low. The reaction temperature is preferably 20 to 200° C., more preferably 40 to 150° C. When the temperature is lower than this range, the conversion of esterification becomes low and when the temperature is higher than the range, by-products are yielded in a large amount. The reaction time is preferably 2 to 50 hours, more preferably 4 to 30 hours. When the reaction time is shorter than this range, the reaction becomes incomplete, and even if the reaction is effected for a period longer than the range, the yield is not increased, so that such a long term reaction is not economical.

When an organic acid per se is used as one of the starting materials in the esterification reaction, the water produced by the reaction may or may not be removed from the system. When the water is to be removed, it is sufficient to effect the reaction using an azeotropically dehydratable solvent such as toluene, xylene, methyl isobutyl ketone or the like and a means such as a Dean-Stark tube or the like capable of allowing the reaction to proceed while removing the water from the system, or the like. Moreover, the reaction may be effected under reduced pressure in order to accelerate the dehydration.

The aryl ester compound which is the component (B) of the epoxy resin composition of this invention includes further aryl ester compounds represented by the general formula (5) as preferable ones:

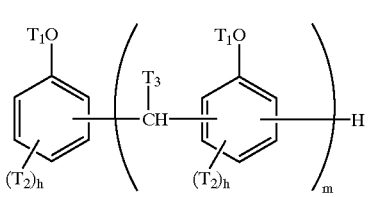

(5)

wherein m represents the average number of the repeated units and is a value of 1 to 10; each $T_1$ represents independently a hydrogen atom or an aromatic ring-free acyl group having 1 to 20 carbon atoms, provided that the case where all $T_1$, groups are hydrogen atoms is excluded; each $T_2$ represents independently a hydrogen atom, an alkyl group having 1 to 10 carbon atoms or a cycloalkyl group having 5 to 7 carbon atoms; h represents an integer of 1 to 3, provided that when h is 2 or 3, $T_2$'s may be the same as or different from one another in one and the same ring; and each $T_3$ represents independently a hydrogen atom, an alkyl group having 1 to 10 carbon atoms, an aryl group having 6 to 20 carbon atoms or an aralkyl group having 7 to 20 carbon atoms.

The aryl ester compound of the general formula (5) can be produced by esterifying a novolak type polyphenol compound as the starting material. The novolak type polyphenol compound used as the starting material is prepared according to a conventional method for producing a novolak type phenol resin, for example, by polycondensing phenols with aldehydes using as a catalyst an inorganic acid such as hydrochloric acid, phosphoric acid, sulfuric acid or the like; an organic acid such as benzenesulfonic acid, toluene-sulfonic acid, oxalic acid or the like; or a metal salt such as zinc acetate or the like.

The phenols include phenol; o-, m- and p-isomers of monoalkylphenols such as cresol, n-propylphenol, isopropylphenol, n-butylphenol, isobutylphenol, t-butylphenol, octylphenol, nonylphenol and the like; various isomers of multi-substituted alkylphenols, representatives of which are xylenol, diisopropylphenol, methylbutylphenol, di-t-butylphenol, di-t-amylphenol, 2,3,5-trimethylphenol and the like; and o-, m- and p-isomers of cycloalkylphenols, representatives of which are cyclopentylphenol, cyclohexylphenol, cyclohexylcresol and the like. These may be used alone or in admixture of two or more.

The aldehydes include formaldehyde; alkylaldehydes, representatives of which are acetaldehyde, propionaldehyde, butyraldehyde, pentylaldehyde and the like; arylaldehydes such as benzaldehyde, naphthaldehyde and the like; and aralkylaldehydes such as 2-methyl-3-(iso-propenylphenyl) propionaldehyde, 2-methyl-3-(t-butylphenyl) propionaldehyde and the like.

In the general formula (5), $T_1$'s may be acyl groups in (m+1) places on average per one molecule (in this case, the acylation percentage is taken as 100%), but $T_1$'s are such that the acylation percentage is any value in other cases than where all $T_1$'s are hydrogen atoms (in this case, the acylation percentage is 0%). In order to achieve the purpose of low dielectric constant and low dielectric loss tangent in this invention, the acylation percentage is preferably at least 30%, more preferably at least 50%.

In the general formula (5), the average number (m) of the repeated units is 1 to 10, preferably 1 to 5. When the average number of the repeated units is more than 10, the viscosity of the whole system combined with the epoxy resin is increased, so that the workability in the preparation of a laminate is deteriorated. When the average number of the repeated units is less than 1, the cure reaction with the epoxy resin is incomplete, or even if cure reaction is possible, the possibility that the heat resistance of the cured product is remarkably deteriorated is high.

The esterification of the novolak polyphenol compound which is used as the starting material for obtaining the aryl ester compound of the general formula (5) can be conducted in the same manner as in the esterification for obtaining the compound of the general formula (3); however, the organic acid or its derivatives is limited to an aromatic ring-free organic acid having 1 to 20 carbon atoms or an acid halide or anhydride thereof.

The epoxy resin used as the component (A) in this invention means a known compound having at least two epoxy groups in one molecule, and the chemical structure of the compound is not critical. Examples of the compound include difunctional type epoxy compounds such as diglycidyl ether of bisphenol A, diglycidyl ether of tetrabromobisphenol A; trifunctional epoxy compounds such as glycidyl ether of tris(4-hydroxyphenyl)methane and glycidyl ether of 1,1,1-tris(4-hydroxyphenyl)ethane; polyfunctional type epoxy compounds such as glycidyl ether of phenol novolak, glycidyl ether of cresol novolak, glycidyl ether of a novolak obtained by dehydration-condensation of phenols with hydroxyarylaldehydes, glycidyl ether of poly(4-hydroxystyrene), glycidyl ether of phenol-modified polybutadiene, glycidyl ether of phenol-dicyclopentadiene adduct and glycidyl ether of bisphenol A novolak; mixtures of at least two epoxy resins; and the like.

The epoxy resin (A) is preferably an epoxy compound represented by the general formula (6):

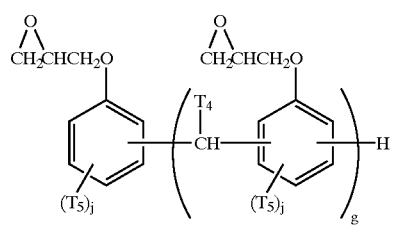

(6)

wherein g represents the average number of the repeated units and is a value of 1 to 10; each $T_4$ represents a hydrogen atom or an alkyl group having 1 to 10 carbon atoms; each $T_5$ represents an alkyl group having 1 to 10 carbon atoms or a cycloalkyl group having 5 to 10 carbon atoms, provided that at least one $T_5$ is an alkyl group having 4 to 10 carbon atoms or a cycloalkyl group having 5 to 7 carbon atoms in one and the same ring; j represents an integer of 1 to 3, provided that when j is 2 or 3, $T_5$'s may be the same as or different from one another in one and the same ring.

The epoxy compound of the general formula (6) can be synthesized by such a known method as dehydrohalogenation of a novolak type polyphenol compound and epihalohydrin with a base.

The novolak type polyphenol compound which is used as the starting material for the epoxy compound of the general formula (6) is produced, for example, by polycondensation of substituted phenols with aldehydes using as a catalyst an inorganic acid such as hydrochloric acid, phosphoric acid, sulfuric acid or the like; an organic acid such as benzenesulfonic acid, toluenesulfonic acid, oxalic acid or the like; or a metal salt such as zinc acetate or the like.

The substituted phenols mean monophenols having at least one alkyl group having 4 to 10 carbon atoms or at least one cycloalkyl group having 5 to 7 carbon atoms in one molecule and includes specifically o-, m- and p-isomers of alkylphenols, representatives of which are n-butylphenol, isobutylphenol, t-butylphenol, octylphenol, nonylphenol, methylbutylphenol, di-t-butylphenol, di-t-amylphenol and the like; and o-, m- and p-isomers of cycloalkylphenols, representatives of which are cyclopentylphenol, cyclohexylphenol, cyclohexylcresol and the like; and these may be used alone or in admixture of two or more.

Examples of the aldehydes include alkylaldehydes, representatives of which are formaldehyde, acetaldehyde, propionaldehyde, butyraldehyde, pentylaldehyde and the like.

In the general formula (6), the average number (g) of the repeated units is 1 to 10, preferably 1 to 5 on average. When the average number (g) of the repeated units is more than 10, the viscosity as an epoxy resin increases, so that the workability in the preparation of a laminate is deteriorated. Moreover, when the average number (g) of the repeated units is less than 1 the cure reaction is remarkably deteriorated.

Examples of the epoxy compound of the general formula (6) include glycidyl ether of 2-t-butyl-5-methylphenol novolak, glycidyl ether of cyclohexylphenol novolak, glycidyl ether of octylphenol novolak, diglycidyl ether of 1,1-(4-hydroxy-5-t-butyl-2-methylphenyl)butane, and the like.

The epoxy resin (A) of this invention may be an epoxy resin obtained by previously reacting an epoxy resin with a halogen-containing bisphenol compound represented by the general formula (7):

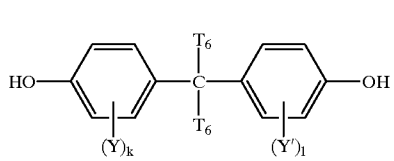

(7)

wherein $T_6$ represents a hydrogen atom or a methyl group and two $T_6$'s may be the same as or different from each other; Y and Y' represent halogen atoms and may be the same as or different from each other; and each of k and l is independently an integer of 1 to 4.

The halogen-containing bisphenol compound of the general formula (7) includes specifically tetrabromobisphenol A, tetrachlorobisphenol A, tetraiodobisphenol A, tetrabromobisphenol F, tetrachlorobisphenol F and the like, and tetrabromobisphenol A is preferably used from the viewpoint of economy and efficient flame-retardation.

The reaction of the epoxy resin with the halogen-containing bisphenol compound of the general formula (7) in this invention may be conducted in a manner known per se.

For example, the above components can be allowed to react in the presence of a basic catalyst such as triphenylphosphine, imidazole or the like. This reaction makes it possible to control the glass transition temperature based on a change in distance between cross-linking sites and to impart a flame-retardance due to a halogen-containing compound without being accompanied by volatilization of low molecular weight materials during curing.

The above two components may be used in any proportion, and it is preferable to mix the two components so that the proportion of the OH groups in the halogen-containing bisphenol compound becomes 0.05 to 0.75 mole per 1 mole of the epoxy group in the epoxy resin and then subjecting them to reaction.

Moreover, it is preferable to mix the epoxy resin (A) with the aryl ester compound (B) so that the ratio of the number of moles of the acyl groups in the aryl ester compound to the number of moles of the epoxy groups in the epoxy resin becomes 0.3:1 to 1.5:1, and this ratio is more preferably 0.5:1 to 1.2:1. When said ratio is outside this range, a failure of curing is caused and good cured product is not obtained.

The cure accelerator in this invention is a conventional compound capable of accelerating the cure reaction between the epoxy resin and the curing agent and examples thereof include imidazoles such as 2-ethyl-4-methylimidazole and 4-methylimidazole; tertiary amines such as triethylamine, benzyldimethylamine and 1,4-diaza-bicyclo [2.2.2] undecene; quaternary ammonium salts such as tetra-n-butylammonium bromide and tetra-n-amylammonium bromide; phosphorus compounds such as triphenylphosphine; and the like. The proportion of the cure accelerator is preferably 0.05 to 3% by weight based on the weight of the resin composition.

It is also possible to use other thermosetting resins than the epoxy resin or a thermoplastic resin having a functional group, in such a proportion that the effect of this invention is not damaged. Specifically, a cyanate resin, a maleimide resin, a glycidyl-modified polybutadiene, maleic anhydride-modified polyethylene or the like may be used.

In this invention, known additives such as flame retardant, surface-treating agent and the like may be added to the epoxy resin composition depending upon the purposes.

The flame retardant includes antimony trioxide, aluminum hydroxide, red phosphorus and the like, and the surface-treating agent includes a silane-coupling agent.

The preparation of the copper-clad laminate of this invention can be conducted according to a known method. That is to say, a substrate is impregnated with the above epoxy resin composition or with a resin varnish prepared by dissolving the above epoxy resin composition in an organic solvent, the impregnated substrate is heat-treated to prepare a prepreg, a copper foil is placed on the prepreg and the resulting assembly is thermoformed to prepare a copper-clad laminate.

The organic solvent used includes acetone, methyl ethyl ketone, methyl isobutyl ketone, ethylene glycol monomethyl ether, propylene glycol monomethyl ether, toluene, xylene, N,N-dimethylformamide, dioxane, tetrahydrofuran and the like, and these solvents may be used alone or in admixture of two or more.

The substrate to be impregnated with the epoxy resin composition or a varnish of the epoxy resin composition includes woven fabrics, non-woven fabrics and mats composed of inorganic or organic fibers such as glass fibers, polyester fibers, polyamide fibers and the like; paper; and the like, and these may be used alone or in combination.

The conditions for the heat-treatment for obtaining the prepreg may be varied depending upon the kind and amount of the solvent, the catalyst added and the various additives; however, it is preferable to conduct the heat-treatment at a temperature of 80° to 220° C. for a period of 3 to 30 minutes.

The thermoforming is conducted, for example, by heat-press molding at a temperature of 150° to 300° C. at a molding pressure of 10 to 100 kg/cm$^2$ for a period of 20 to 300 minutes.

DESCRIPTION OF THE PREFERRED EMBODIMENTS

Examples of this invention are shown below; however, this invention should not be construed to be limited thereto. In the Examples, the epoxy equivalent is defined as the molecular weight of the epoxy resin per one epoxy group, and the OH equivalent is defined as the molecular weight of the polyhydric phenol compound per one OH group.

Synthetic Example 1

The present Synthetic Example relates to a process for producing glycidyl ether of 2-t-butyl-5-methylphenol novolak which is the starting material of the epoxy resin used in the epoxy resin composition of this invention.

In a 5-liter, four-necked, round-bottomed flask equipped with a thermometer, a stirring means, a condenser and a dropping tube were placed 2231.0 g (13.58 OH mol eq.) of 2-t-butyl-5-methylphenol, 12.9 g (0.068 mol) of p-toluenesulfonic acid and 223.2 g of deionized water, and the temperature was elevated to 100° C., after which 218.4 g (2.715 mols) of 37% formalin was dropwise added thereto over two hours. Thereafter, the resulting mixture was kept at 100° C. for two hours to allow the reaction to proceed. Thereafter, the reaction mixture was cooled to 80° C. and neutralized with 27.7 g (0.069 mol) of a 10% aqueous NaOH solution. The organic layer obtained was washed twice with 700 g of deionized water. After the washing, the organic layer was concentrated under reduced pressure (180° C./10 mmHg/1 hour) to obtain 857.2 g of a resinous product. The OH equivalent of the resinous product obtained was 176.0 g/eq.

In a 2-liter, four-necked, round-bottomed flask equipped with a thermometer, a stirring means and a separating tube-attached condenser were placed 246.4 g (1.4 OH mol eq.) of the resinous product thus obtained, 906.5 g (9.8 mols) of epichlorohydrin, 453.3 g of dimethyl sulfoxide and 14.0 g of deionized water, and thereafter, 108.31 g (1.316 mols) of a 48.6% aqueous NaOH solution was dropwise added thereto over five hours at 49° C. at 42 Torr. During this period, the azeotropically distilled epichlorohydrin and water were cooled to be liquefied while the temperature was kept at 49° C., and the reaction was allowed to proceed while the organic layer was returned to the reaction system.

After completion of the reaction, unreacted epichlorohydrin was removed by concentration under reduced pressure, and an epoxidized product containing a salt produced as a by-product and dimethyl sulfoxide was dissolved in methyl isobutyl ketone, after which the salt and dimethyl sulfoxide were removed by washing with warm water. The solvent was removed under reduced pressure, to obtain 304.9 g of an epoxy resin.

The epoxy equivalent of the epoxy resin thus obtained was 256 g/eq. As a result of measurement of infrared absorption spectrum, it was confirmed that absorption of phenolic OH at 3,200–3,600 cm$^{-1}$ disappeared and absorption of epoxide was confirmed at 1,240 and 910 cm$^{-1}$.

Synthesis Example 2

The present Synthesis Example relates to a process for producing an epoxy-terminated resin by addition-reaction between the epoxy resin obtained in Synthesis Example 1 and tetrabromobisphenol A and diglycidyl ether of tetrabromobisphenol A.

In a 300-ml, four-necked, round-bottomed flask equipped with a thermometer, a condenser and a stirring means were placed 62.0 g of the epoxy resin obtained in Synthesis Example 1, 25.3 g of diglycidyl ether of tetrabromobisphenol A (Sumi-®epoxy ESB-400T, a trade name of Sumitomo Chemical Co., Ltd., epoxy equivalent: 403 g/eq) and 12.7 g of tetrabromobisphenol A and heated at 110° C. to be melted. Thereafter, a solution of 40 mg of triphenylphosphine (4×10$^{-4}$% by weight based on the resin) in 2.25 g of methyl ethyl ketone was added to the molten mixture, and the resulting mixture was kept at 110° C. for four hours to allow the addition reaction between the epoxy group and the phenolic OH group to proceed. After the reaction, the reaction system was cooled to 90° C. and 22.75 g of methyl ethyl ketone was dropwise added thereto, to obtain 123.9 g of a resin solution having a resin solid content of 80.62% by weight. The epoxy equivalent of the resin obtained was 399.0 g/eq.

Synthesis Example 3

The present Synthesis Example relates to a process for producing an epoxy-terminated resin by addition reaction between the epoxy resin obtained in Synthesis Example 1 and tetrabromobisphenol A and diglycidyl ether of tetrabromobisphenol A.

In a 300-ml, four-necked, round-bottomed flask equipped with a thermometer, a condenser and a stirring means were placed 47.4 g of the epoxy resin obtained in Synthesis Example 1, 42.7 g of diglycidyl ether of tetrabromobisphenol A (Sumiepoxy ESB-400, a trade name of Sumitomo Chemical Co., Ltd., epoxy equivalent: 403 g/eq.) and 9.9 g of tetrabromobisphenol A, and heated at 110° C. to be melted. Thereafter, a solution of 40 mg of triphenylphosphine (4×10$^{-4}$% by weight based on the resin) in 2.25 g of methyl ethyl ketone was added to the molten mixture and the resulting mixture was kept at 110° C. for four hours to allow the addition reaction between the epoxy group and the phenolic OH group to proceed. After the reaction, the reaction system was cooled to 90° C. and 22.75 g of methyl ethyl ketone was dropwise added thereto, to obtain 123.7 g of a resin solution having a resin solid content of 80.5% by weight. The epoxy equivalent of the resin obtained was 385.0 g/eq.

Synthesis Example 4

The present Synthesis Example relates to a process for producing 2,4,4-trimethyl-2-(2,4-dihydroxyphenyl)-7-hydroxychroman (CAS No. 26505-28-2) which is the starting polyhydric phenol for the aryl ester compound of this invention.

In a 5-liter, four-necked round-bottomed flask equipped with a thermometer, a stirring means, a condenser and a dropping funnel were placed 1,000.0 g (9.1 mols) of resorcinol, 6.9 g (0.036 mol) of p-toluenesulfonic acid, 330.0 g of methanol and 176.0 g (3.0 mols) of acetone, and the temperature was elevated to 65° C. After the mixture was kept at 65° C. for nine hours, 750 g of deionized water was added to the mixture and the resulting mixture was kept at 40° C. for three hours. Thereafter, the crystals precipitated were collected by filtration and washed with deionized water. The crude crystals obtained were dissolved in methanol, and then deionized water was dropwise added to the solution to effect recrystalli-zation. The resulting crystals were collected by filtration and dried under reduced pressure. The yield was 265 g. It was confirmed by $^1$H-NMR and IR that the crystals obtained were of the objective compound.

Synthesis Example 5

The present Synthesis Examples relates to a process for producing 4-[1', 2', 3', 4', 4'a,9'a-hexahydro-6'-hydroxyspiro(cyclohexane-1,9'-xanthene)-4'a-yl]resorcinol (CAS No. 138446-23-8) which is a compound represented by the general formula (3) in which n is 1, P is a hydrogen atom, $R_1$ and $R_2$ are pentamethylene chains forming a 6-membered ring together with the carbon atom to which $R_1$, and $R_2$ are attached, $R_4$ and $R_5$ are tetramethylene chains forming a 6-membered ring together with the carbon atoms to which $R_4$ and $R_5$ are attached, $R_3$ is a hydrogen atom and each Z is a hydrogen atom.

In a 5-liter, four-necked round-bottomed flask equipped with a thermometer, a stirring means, a condenser and a dropping funnel were placed 880.0 g (8.0 mols) of resorcinol, 73.5 g (0.39 mol) of p-toluenesulfonic acid, 1,200.0 g of methanol and 495.0 g (5.0 mols) of cyclohexanone, and the temperature was elevated to 60° C. After the mixture was kept at 60° C. for 20 hours, 800 g of deionized water was added to the mixture and the resulting mixture was kept at 40° C. for three hours, after which the crystals precipitated were collected by filtration and washed with deionized water. The crude crystals obtained were dissolved in methanol and thereafter deionized water was dropwise added to the solution to effect recrystallization. The crystals formed were collected by filtration and dried under reduced pressure. The yield was 339 g. It was confirmed by $^1$H-NMR, IR and GPC that the crystals were of the objective compound.

Synthesis Example 6

The present Synthesis Example relates to a process for producing a condensation product of resorcinol with acetone which is the starting material for the aryl ester compound of this invention.

In a 2-liter, four-necked, round-bottomed flask equipped with a thermometer, a stirring means, a condenser and a dropping funnel were placed 220.2 g (2.0 mols) of resorcinol, 200.0 g of toluene and 232.3 g (4.0 mols) of acetone, and the temperature was elevated to 30° C. A solution of 76.1 g (0.40 mol) of p-toluenesulfonic acid in 100 g of water was added to the resulting mixture and the temperature was elevated to 50° C., after which the mixture was kept at this temperature for 40 hours. After neutralization, the reaction mixture was diluted with methyl isobutyl ketone and washed with water, after which the solvent was removed by distillation under reduced pressure, to obtain 344 g of a resinous product. It was confirmed by $^1$H-NMR, IR and GPC that the product was a mixture comprising as the main component a compound represented by the structural formula (8):

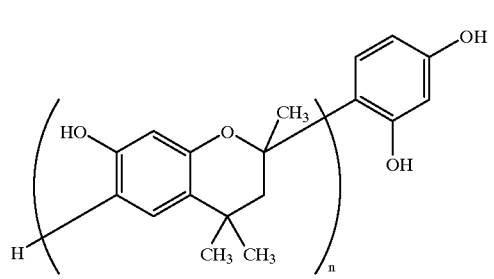

(8)

Synthesis Example 7

The present Synthesis Example relates to a process for producing a novolak type polyphenol compound which is used as the starting material for an aryl ester compound represented by the general formula (5) in which $T_2$ is a cyclohexyl group, h is 1 and $T_3$ is a hydrogen atom.

In a 0.5-liter, four-necked, round-bottomed flask equipped with a thermometer, a stirring means and a condenser were placed 317.4 g (1.8 mols) of cyclohexylphenol (mixture of o- and p-isomers) and 300.0 g of toluene, and the temperature was elevated to 80° C. After the addition of 20.6 g (0.108 mol) of p-toluenesulfonic acid, 109.5 g (1.35 mols) of 37% formalin was dropwise added to the mixture through a dropping tube over three hours. The temperature was elevated to 90° C. and the mixture was kept at this temperature for nine hours. After the reaction, the reaction mixture was allowed to stand and the aqueous layer formed was removed, and the remaining organic layer was washed with 500 g of deionized water six times. The organic layer washed was concentrated under reduced pressure (170° C./5 mmHg/0.5 hour) to obtain 305.4 g of a resinous product. The OH equivalent of the resinous product obtained was 185.9 g/eq.

Synthesis Example 8

The present Synthesis Example relates to a process for producing a novolak type polyphenol compound which is used as the starting material for an aryl ester compound represented by the general formula (5) in which $T_2$ is a t-octyl group, h is 1 and $T_3$ is a hydrogen atom.

In a 0.5-liter, four-necked, round-bottomed flask equipped with a thermometer, a stirring means and a condenser were placed 165.0 g (0.8 mol) of 4-t-octylphenol and 120.0 g of toluene and the temperature was elevated to 80° C. After the addition of 2.85 g (0.015 mol) of p-toluenesulfonic acid and 12.0 g of deionized water, 48.7 g (0.60 mol) of 37% formalin was dropwise added to the mixture through a dropping tube over two hours. The resulting mixture was heated under reflux for two hours. After the reaction, the reaction mixture was diluted with 120.0 g of toluene, neutralized with 6.0 g of a 10% aqueous NaOH solution and thereafter washed twice with 200 g of deionized water. The organic layer after the washing was concentrated under reduced pressure (170° C./5 mmHg/0.5 hour) to obtain 136.2 g of a resinous product. The OH equivalent of the resinous product obtained was 216.0 g/eq.

Synthesis Example 9

The present Synthesis Example relates to a process for producing a compound represented by the general formula (5) in which $T_1$ is an acetyl group or a hydrogen atom, $T_2$ is a cyclohexyl group, h is 1 and $T_3$ is a hydrogen atom.

In a 0.5-liter, four-necked, round-bottomed flask equipped with a thermometer, a stirring means, a dropping tube and a condenser were placed 94.0 g (0.5 OH mol eq.) of the product obtained in Synthesis Example 7, 115.0 g of methyl isobutyl ketone and 0.47 g of pyridine, and then the temperature was elevated to 70° C., after which 51 g (0.5 mol) of acetic anhydride was dropwise added thereto over 1.5 hours. Thereafter, the temperature was elevated to 90° C., at which temperature the mixture was kept for four hours to allow the reaction to proceed. The reaction mixture was diluted with 345 g of methyl isobutyl ketone, neutralized with a 5% aqueous sodium hydrogencarbonate solution and then washed, and thereafter, further washed twice with 200 g of deionized water. The organic layer after the washing was concentrated under reduced pressure (150° C./5 mmHg/1 hour) to obtain 108.1 g of a resinous product. The average esterification percentage of the $T_1$ portion was 54.9% as measured by $^1$H-NMR.

Synthesis Example 10

The present Synthesis Example relates to a process for producing a compound represented by the general formula (5) in which $T_1$ is an acetyl group or a hydrogen atom, $T_2$ is a t-octyl group, h is 1 and $T_3$ is a hydrogen atom.

In a 0.5-liter, four-necked, round-bottomed flask equipped with a thermometer, a stirring means, a dropping tube and a condenser were placed 109 g (0.5 OH mol eq.) of the product obtained in Synthesis Example 8, 130.0 g of methyl isobutyl ketone and 0.55 g of pyridine, and the temperature was then elevated to 70° C. After the dropwise addition of 51 g (0.5 mol) of acetic anhydride over 1.5 hours, the temperature was elevated to 90° C., at which temperature the mixture was kept for two hours to allow the reaction to proceed. The reaction mixture was diluted with 173 g of methyl isobutyl ketone, neutralized with a 5% aqueous sodium hydrogencarbonate solution and washed, and then further washed with 200 g of deionized water. The organic layer after the washing was concentrated under reduced pressure (140° C./5 mmHg/1 hour) to obtain 122.7 g of a resinous product. The average esterification percentage of the $T_1$ portion was 70.1% as measured by $^1$H-NMR.

Synthesis Example 11

The present Synthesis Example relates to a process for producing a compound of the general formula (5) in which $T_1$ is an acetyl group or a hydrogen atom, $T_2$ is a methyl group, h is 1 and $T_3$ is a hydrogen atom.

In a 0.5-liter, four-necked, round-bottomed flask equipped with a thermometer, a stirring means, a dropping tube and a condenser were placed 96.0 g (0.8 OH mol eq.) of o-cresol novolak, 129.6 g of methyl isobutyl ketone and 0.48 g of pyridine, and the temperature was then elevated to 70° C. After the dropwise addition of 81.6 g (0.8 mol) of acetic anhydride over 1.5 hours, the resulting mixture was kept at 70° C. for four hours to allow the reaction to proceed. The reaction mixture was diluted with 172.8 g of methyl isobutyl ketone, neutralized with a 5% aqueous sodium hydrogencarbonate, washed and then further washed with 200 g of deionized water. The organic layer after the washing was concentrated under reduced pressure (150° C./5 mmHg/1 hour) to obtain 119.0 g of a resinous product. The average esterification percentage of the $T_1$ portion was 74.4% as measured by $^1$H-NMR.

Synthesis Example 12

The present Synthesis Example relates to a process for producing a compound represented by the general formula (5) in which $T_1$ is an acetyl group or a hydrogen atom, $T_2$ is a hydrogen atom, h is 1 and $T_3$ is a hydrogen atom.

In a 0.5-liter, four-necked, round-bottomed flask equipped with a thermometer, a stirring means, a dropping tube and a condenser were placed 108.0 g (0.9 OH mol eq.) of phenol novolak, 135.0 g of methyl isobutyl ketone and 0.49 g of pyridine, and the temperature was then elevated to 70° C. After the dropwise addition of 96.9 (0.95 mol) of acetic anhydride over two hours, the resulting mixture was kept at 70° C. for four hours to allow the reaction to proceed. The reaction mixture was diluted with 180.0 g of methyl isobutyl ketone, neutralized with a 5% aqueous sodium hydrogencarbonate solution, washed, and then further washed with 200 g of deionized water. The organic layer after the washing was concentrated under reduced pressure (150° C./10 mmHg/1 hour) to obtain 127.0 g of a resinous product. The average esterification percentage of the $T_1$ portion was 96.5% as measured by $^1$H-NMR.

EXAMPLE 1

The present Example relates to a process for producing an acetic acid ester of 2,4,4-trimethyl-2-(2,4-dihydroxyphenyl)-7-hydroxychroman [aryl ester (a)] which is a compound of the general formula (3) in which $R_1$, $R_2$, and $R_5$ are methyl groups, $R_3$ and $R_4$ are hydrogen atoms, Z is a hydrogen atom or an acetyl group, P is a hydrogen atom, i is 0, and n is 1.

In a 2.0-liter, four-necked, round-bottomed flask equipped with a thermometer, a stirring means, a condenser and a dropping funnel were placed 100.0 g (1.00 OH mol eq.) of the 2,4,4-trimethyl-2-(2,4-dihydroxyphenyl)-7-hydroxychroman obtained in Synthesis Example 4, 106.1 g (1.05 mols) of triethylamine and 568.0 g of methyl isobutyl ketone, and the temperature was then elevated to 70° C., after which 107.1 g (1.05 mols) of acetic anhydride was dropwise added to the mixture over two hours. The resulting mixture was kept at 70° C. for four hours, and then washed with water, after which the aqueous layer formed was removed. The solvent was removed by distillation under reduced pressure (150° C./<5 mmHg), to obtain 139.6 g of a resinous product. The resinous product was allowed to stand, during which the product was gradually crystallized. The esterification percentage was 100% as measured by a high performance liquid chromatography (triester form 100%) [melting point was 121° C. as measured by a differential scanning calorimeter (DSC)].

It was confirmed from the following analytical values that the resinous product was the objective compound:
Analytical Values Infrared absorption spectrum measurement (KBr tablet method)/2970, 1760 (C=O), 1605, 1580, 1490, 1420, 1365, 1200, 1145, 1125, 1100, 1035, 1010, 990, 900 cm$^{-1}$.

Proton nuclear magnetic resonance spectrum (solvent: CDCl$_3$)/δ(ppm) 0.79 (s, 3H, methyl), 1.30 (s, 3H, methyl), 1.64 (s, 3H, methyl), 2.13 (d, 1H, methylene), 2.24 (s, 3H, acetyl), 2.29 (s, 3H, acetyl), 2.35 (s, 3H, acetyl), 2.53 (d, 1H, methylene), 6.62–7.46 (m, 6H, aryl)

EXAMPLE 2

The present Example relates to a process for producing benzoic acid ester of 2,4,4-trimethyl-2-(2,4-dihydroxyphenyl)-7-hydroxychroman [aryl ester (b)] which is a compound represented by the general formula (3) in which $R_1$, $R_2$, and $R_5$ are methyl groups, $R_3$ and $R_4$ are hydrogen atoms, z is a hydrogen atom or a benzoyl group, P is a hydrogen atom, i is 0, and n is 1.

In a 1.0-liter, four-necked, round-bottomed flask equipped with a thermometer, a stirring means, a condenser and a dropping funnel were placed 70.0 g (0.70 OH mol eq.) of the 2,4,4-trimethyl-2-(2,4-dihydroxyphenyl)-7-hydroxychroman (CAS No. 26505-28-2) obtained in Synthesis Example 4, 77.8 g (0.77 mol) of triethylamine and 325.0 g of methyl isobutyl ketone, and the temperature was then elevated to 70° C., after which 108.2 g (0.77 mol) of benzoyl chloride was dropwise added thereto over two hours. The mixture was kept at 70° C. for four hours, and then washed with water, after which the aqueous layer formed was removed. The remaining oily layer was thereafter cooled to room temperature, upon which crystals were precipitated. The mixture was allowed to stand overnight, and the crystals were collected by filtration, washed with pure water and then with cooled methanol and thereafter dried at 80° C. under reduced pressure, to obtain 133.6 g of white crystals. The esterification percentage was 100% (triester form 100%) as measured by a high performance liquid chromatography.

It was confirmed from the following analytical values that the crystals were of the objective compound.
Analytical Values Infrared absorption spectrum measurement (KBr tablet method)/2950, 1740 (C=O), 1600, 1490, 1450, 1420, 1240, 1150, 1060, 1020, 700 cm$^{-1}$.

Proton nuclear magnetic resonance spectrum (solvent:CDCl$_3$)δ(ppm) 0.93 (s, 3H, methyl), 1.30 (s, 3H, methyl), 1.74 (s, 3H, methyl), 2.12 (d, 1H, methylene), 2.63 (d, 1H, methylene), 6.82–7.26 (m, 6H, aryl), 7.48–7.66 (m, 10H, phenyl of benzoyl), 8.14–8.26 (m, 5H, phenyl of benzoyl)

EXAMPLE 3

The present Example relates to a process for producing an acetic acid ester of 4-[1',2',3',4',4'a,9'a-hexahydro-6'-hydroxyspiro (cyclohexane-1,9'-xanthene)-4'a-yl]resorcinol [aryl ester (c)] which is a compound represented by the general formula (3) in which n is 1, each P is a hydrogen atom, $R_1$ and $R_2$ are pentamethylene chains forming a ring together with the carbon atom to which $R_1$ and $R_2$ are attached, $R_4$ and $R_5$ are tetramethylene chains forming a 6-membered ring together with the carbon atoms to which $R_4$ and $R_5$ are attached and some of Z's are acetyl groups and the other are hydrogen atoms.

In a 1.0-liter, four-necked, round-bottomed flask equipped with a thermometer, a stirring means, a condenser and a dropping funnel were placed 60.0 g (0.41 OH mol eq.) of the 4-[1', 2', 3', 4', 4'a, 9'a-hexahydro-6'-hydroxyspiro (cyclohexane-1,9'-xanthene)-4'a-yl]resorcinol (CAS No. 138446-23-8) obtained in Synthesis Example 5, 45.5 g (0.45 mol) of triethylamine and 179.2 g of methyl isobutyl ketone, and the temperature was then elevated to 80° C., after which 45.9 g (0.45 mol) of acetic anhydride was dropwise added to the mixture over one hour. The mixture was kept at 90° C. for four hours and then washed with water, after which the aqueous layer formed was removed. The solvent was removed by distillation under reduced pressure (150° C./<5 mmHg), to obtain 72.9 g of a resinous product. The esterification percentage was 79.2% as measured by a high performance liquid chromatography (diester form 62.3%, triester form 37.7%).

It was confirmed from the following analytical values that the resinous product was the objective compound:

Analytical Values

Infrared absorption spectrum measurement (KBr tablet method)/2930, 1760 (C=O), 1610, 1585, 1490, 1420, 1370, 1210, 1150, 1125, 1015, 755 $cm^{-1}$.

Proton nuclear magnetic resonance (solvent: $CDCl_3$)/δ (ppm) 0.65–1.82 and 3.11–3.24 (m, 19H, cycloalkyl), 2.13–2.41 (m, 7.13H, acetyl), 5.99–7.32 (m, 6H, aryl), 8.52 (s, 0.62H, hydroxy)

EXAMPLE 4

The present Example relates to a process for producing acetic acid ester [aryl ester (d)] of the poly-hydric phenol obtained in Synthetic Example 5 which ester is the aryl ester compound of this invention.

In a 2-liter, four-necked, round-bottomed flask equipped with a thermometer, a stirring means, a condenser and a dropping funnel were placed 100.0 g (0.528 mol) of the polyhydric phenol obtained in Synthesis Example 6, 64.0 g (0.632 mol) of triethylamine and 285.0 g of methyl isobutyl ketone, and the temperature was then elevated to 70° C., after which 64.4 g (0.632 mol) of acetic anhydride was dropwise added to the mixture over one hour. The temperature was then elevated to 90° C. and the mixture was kept at 90° C. for five hours to allow the reaction to proceed, after which the reaction mixture was diluted with methyl isobutyl ketone and washed with water. The aqueous layer formed was removed and the solvent was removed by distillation under reduced pressure to obtain 112 g of a golden resinous product. Since it was confirmed by infrared absorption spectrum measurement that absorption of OH group disappeared at 3,100–3,600 $cm^{-1}$, and absorption of carbonyl group appeared at 1,760 $cm^{-1}$, the esterification percentage was decided as approximately 100%.

Analytical Values

Infrared absorption spectrum measurement (NaBr plate)/ 2970, 1760 (C=O), 1620, 1580, 1490, 1420, 1370, 1200, 1150, 1120, 900, 760 $cm^{-1}$.

EXAMPLES 5 TO 16

Diglycidyl ether of bisphenol A (Sumi-®epoxy ELA-128, a trade name of Sumitomo Chemical Co., Ltd., epoxy equivalent: 186 g/eq) and the epoxy resins obtained in Synthesis Examples 1 and 2 were used as the epoxy resins and were blended with the compounds obtained in Examples 1, 2, 3 and 4 and 2-ethyl-4-methylimidazole (cure accelerator) (Curesol 2E4MZ, a trade name of Shikoku Kasei Kogyo Kabushiki Kaish) in the amounts shown in Table 1 and the resulting mixture was dissolved in a solvent to prepare a uniform resin varnish. The resin varnish was subjected to distillation to remove the solvent, and the resin mixture thus obtained was press-molded to obtain a resin cured plate having the predetermined thickness.

The dielectric constant and dielectric loss tangent at 1 GHz of the resin cured plate were determined by setting a sample having electrodes formed on both sides thereof by gold deposition on a Resonant Coaxial Line Model 34A manufactured by Boonton Electronics Company and measuring the resonance frequency and frequency of 6.02 dB down by means of 8573A Network Analyzer manufactured by HEWLETT-PACKARD COMPANY through 85046A S-parameter test set manufactured by HEWLETT-PACKARD COMPANY. The results are shown in Table 1.

TABLE 1

| | Example No. | | | | | |
|---|---|---|---|---|---|---|
| | 5 | 6 | 7 | 8 | 9 | 10 |
| Sumi- ® epoxy ELA-128 | 56.7 | 48.3 | 49.9 | 44.5 | | |
| Epoxy resin of Synthesis Ex. 1 | | | | | 63.8 | 55.7 |
| Epoxy resin of Synthesis Ex. 2 | | | | | | |
| Sumi- ® epoxy ESB-500 | | | | | | |
| Aryl ester (a) | 43.3 | | | | 36.2 | |
| Aryl ester (b) | | 51.7 | | | | 44.3 |
| Aryl ester (c) | | | 50.1 | | | |
| Aryl ester (d) | | | | 55.5 | | |

TABLE 1-continued

|  | Example No. | | | | | |
| --- | --- | --- | --- | --- | --- | --- |
|  | 5 | 6 | 7 | 8 | 9 | 10 |
| Tamanol 758 | | | | | | |
| Dicyandiamide | | | | | | |
| Curesol 2E4MZ | 0.5 | 0.5 | 0.5 | 0.5 | 0.5 | 0.5 |
| Methyl ethyl ketone | 100 | 100 | 100 | 100 | 100 | 100 |
| Dielectric constant (at 1 GHz) | 3.01 | 2.97 | 2.95 | 2.88 | 2.76 | 2.72 |
| Dielectric loss tangent (at 1 GHz) | 0.0138 | 0.0123 | 0.0132 | 0.0115 | 0.0113 | 0.0100 |

|  | Example No. | | | | | |
| --- | --- | --- | --- | --- | --- | --- |
|  | 11 | 12 | 13 | 14 | 15 | 16 |
| Sumi-® epoxy ELA-128 | | | | | | |
| Epoxy resin of Synthesis Ex. 1 | 57.2 | 52.1 | | | | |
| Epoxy resin of Synthesis Ex. 2 | | | 73.3 | 66.2 | 67.6 | 62.4 |
| Sumi-® epoxy ESB-500 | | | | | | |
| Aryl ester (a) | | | 26.7 | | | |
| Aryl ester (b) | | | | 33.8 | | |
| Aryl ester (c) | 42.8 | | | | 32.4 | |
| Aryl ester (d) | | 47.9 | | | | 37.6 |
| Tamanol 758 | | | | | | |
| Dicyandiamide | | | | | | |
| Curesol 2E4MZ | 0.5 | 0.5 | 0.5 | 0.5 | 0.5 | 0.5 |
| Methyl ethyl ketone | 100 | 100 | 100 | 100 | 100 | 100 |
| Dielectric constant (at 1 GHz) | 2.70 | 2.71 | 2.89 | 2.87 | 2.82 | 2.90 |
| Dielectric loss tangent (at 1 GHz) | 0.0122 | 0.0115 | 0.0118 | 0.0104 | 0.0110 | 0.0102 |

EXAMPLES 17 TO 22

Diglycidyl ether of bisphenol A (Sumi-®epoxy ELA-128, a trade name of Sumitomo Chemical Co., Ltd., epoxy equivalent: 186 g/eq) and the epoxy resins obtained in Synthesis Examples 1 and 2 were used as the epoxy resins and blended with the compounds obtained in Synthesis Examples 8 and 10 and 2-ethyl-4-methylimidazole (Curesol 2E4MZ, a trade name of Shikoku Kasei Kogyo Kabushiki Kaisha) (cure accelerator) in the amounts shown in Table 2, and the resulting mixture was dissolved in a solvent to prepare a uniform resin varnish. The resin varnish was subjected to distillation to remove the solvent and the resin mixture thus obtained was press-molded to obtain a resin cured plate having the predetermined thickness.

The dielectric constant and dielectric loss tangent at 1 GHz of the resin cured plate were measured in the same manner as in Examples 5 to 16. The results are shown in Table 2.

Comparative Examples 1 to 4

Diglycidyl ether of bisphenol A (Sumi-®epoxy ELA-128, a trade name of Sumitomo Chemical Co., Ltd.) and an epoxy terminated resin (Sumi-®epoxy ESB-500, a trade name of Sumitomo Chemical Co., Ltd.) obtained by subjecting diglycidyl ether of bisphenol A and tetrabromobisphenol A to addition reaction were used as the epoxy resins in the amounts shown in Table 3; a phenol novolak resin (Tamanol 758, a trade name of Arakawa Kagaku Kogyo Kabushiki Kaisha) or dicyandiamide were used as the curing agents in the amounts shown in Table 3; and 2-ethyl-4-methylimidazole (Curesol 2E4MZ) was used as the cure accelerator in the amount shown in Table 3 to prepare a resin cured plate in the same manner as in Examples 5 to 22, and the dielectric constant and dielectric loss tangent at 1 GHz of the resin cured plate were measured in the same manner as in Examples 5 to 22. The results are shown in Table 3.

TABLE 2

|  | Example No. | | | | | |
| --- | --- | --- | --- | --- | --- | --- |
|  | 17 | 18 | 19 | 20 | 21 | 22 |
| Sumi-® epoxy ELA-128 | 44.7 | 53.4 | | | | |
| Epoxy resin of Synthesis Ex. 1 | | | 52.1 | 60.6 | | |
| Epoxy resin of Synthesis Ex. 2 | | | | | 62.9 | 70.7 |
| Product of Synthesis Ex. 9 | 55.3 | | 47.9 | | 37.1 | |
| Product of Synthesis Ex. 11 | | 46.5 | | 39.4 | | 29.3 |
| Tamanol 758 | | | | | | |
| Curesol 2E4MZ | 0.5 | 0.5 | 0.5 | 0.5 | 1 | 0.5 |
| Methyl ethyl ketone | 100 | 100 | 100 | 100 | 100 | 100 |
| Dielectric constant (at 1 GHz) | 2.97 | 3.06 | 2.82 | 2.87 | 2.82 | 2.88 |
| Dielectric loss tangent (at 1 GHz) | 0.0131 | 0.0145 | 0.006 | 0.0091 | 0.0118 | 0.0126 |

TABLE 3

| | Compatative Example No. | | | |
|---|---|---|---|---|
| | 1 | 2 | 3 | 4 |
| Sumi-® epoxy ELA-128 | 63.7 | 92.5 | | |
| Sumi-® epoxy ESB-500 | | | 83.6 | 97.1 |
| Tamanol 758 | 36.3 | | 16.4 | |
| Dicyandiamide | | 7.5 | | 2.9 |
| Curesol 2E4MZ | 0.1 | 0.2 | 0.2 | 0.2 |
| Methyl ethyl ketone | 100 | 100 | 100 | 100 |
| Dielectric constant (at 1 GHz) | 3.38 | 3.41 | 3.44 | 3.52 |
| Dielectric loss tangent (at 1 GHz) | 0.0207 | 0.0255 | 0.0288 | 0.0279 |

EXAMPLES 23 TO 31

Diglycidyl ether of bisphenol A (Sumi-®epoxy ELA-128, a trade name of Sumitomo Chemical Co., Ltd., epoxy equivalent: 186 g/eq) and the epoxy resins obtained in Synthesis Examples 1, 2 and 3 were used as the epoxy resins and blended with the compounds obtained in Examples 1, 2, 3 and 4, diglycidyl ether of tetrabromobisphenol A (Sumiepoxy ESB-400T, a trade name of Sumitomo Chemical Co., Ltd., epoxy equivalent: 403 g/eq) and 2-ethyl-4-methylimidazole of the cure accelerator (Curesol 2E4MZ, a trade name of Shikoku Kasei Kogyo Kabushiki Kaisha) in the amounts shown in Table 4, and the resulting mixture was dissolved in a solvent to prepare a uniform resin varnish. A glass cloth (KS-1600S962LP, a trade name of KANEBO, LTD.) was impregnated with the resin varnish obtained and treated for 5 to 10 minutes in a hot-air drying means at 150° C. to obtain a prepreg. Five sheets of this prepreg were put on one another and a copper foil (TTAI-treated, 35 μ in thickness, manufactured by Furukawa Circuit Foil, Co., Ltd.) was placed on the resulting assembly. The resulting assembly was press-molded at 170° C. at a pressure of 50 kg/cm² for 120 minutes to obtain a copper-clad laminate having a thickness of 1 mm.

The glass transition temperature (Tg) of the laminate was determined from the inflection point of the thermal expansion curve obtained using a thermal analyzing apparatus DT-30 manufactured by Shimadzu Corp. The dielectric constant and dielectric loss tangent at 1 GHz of the laminate were determined by setting the laminate having electrodes formed on both sides thereof by gold deposition on a Resonance Coaxial Line Model 34A manufactured by Boonton Electronics Company and measuring the resonant frequency and frequency of 6.02 dB down by means of 8573A Network Analyzer manufactured by HEWLETT-PACKARD COMPANY through 85046A S-parameter test set manufactured by HEWLETT-PACKARD COMPANY. The copper foil-peeling strength, boiling water absorption and soldering heat resistance of the laminate were measured according to JIS C-6481. The measurement results are shown in Table 4.

The flame-retardancy tests on Table 4 were carried out based on the UL94 standard and 'Burn' means that the samples were burned.

TABLE 4

| | | Example No. | | | | |
|---|---|---|---|---|---|---|
| | | 23 | 24 | 25 | 26 | 27 |
| Sumi-® epoxy ELA-128 | | 57.1 | | | | |
| Epoxy resin of Synthesis Ex. 1 | | | 64.0 | | | |
| Epoxy resin of Synthesis Ex. 2 | | | | 55.9 | | |
| Epoxy resin of Synthesis Ex. 3 | | | | | 71.9 | |
| Sumi-® epoxy ESB-500 | | | | | | 56.9 |
| Sumi-® epoxy ESB-400T | | | | 17.8 | 1.2 | 19.7 |
| Sumi-® epoxy ESCN-220 | | | | | | |
| Aryl ester (a) | | 42.9 | 36.0 | 26.3 | 26.9 | 23.4 |
| Aryl ester (b) | | | | | | |
| Aryl ester (c) | | | | | | |
| Aryl ester (d) | | | | | | |
| Dicyandiamide | | | | | | |
| Curesol 2E4MZ | | 0.5 | 0.5 | 0.5 | 0.5 | 0.5 |
| Glass transition temp. | °C. | 126 | 134 | 132 | 130 | 122 |
| Copper foil-peeling strength | kg/cm | 1.78 | 1.55 | 1.34 | 1.30 | 1.66 |
| Boiling water absorption (48 hrs) | wt. % | 0.20 | 0.15 | 0.21 | 0.22 | 0.43 |
| Soldering heat resistance (normal state) | | 10 min or more | 10 min or more | 10 min or more | 10 min or more | 10 min or more |
| Dielectric constant (at 1 GHz) | | 4.11 | 3.98 | 4.11 | 4.13 | 4.22 |
| Dielectric loss tangent (at 1 GHz) | | 0.0131 | 0.0112 | 0.0119 | 0.0123 | 0.0132 |
| Flame-retardancy (UL 94) | | Burn | Burn | V-O | V-O | V-O |

TABLE 4-continued

|  |  | Example No. | | | |
|---|---|---|---|---|---|
|  |  | 28 | 29 | 30 | 31 |
| Sumi-® epoxy ELA-128 | | | | | |
| Epoxy resin of Synthesis Ex. 1 | | | | | |
| Epoxy resin of Synthesis Ex. 2 | | | | | |
| Epoxy resin of Synthesis Ex. 3 | | 56.4 | 59.4 | 48.8 | |
| Sumi-® epoxy ESB-500 | | | | | 42.1 |
| Sumi-® epoxy ESB-400T | | 9.7 | 8.0 | 13.8 | 24.2 |
| Sumi-® epoxy ESCN-220 | | | | | |
| Aryl ester (a) | | | | | |
| Aryl ester (b) | | 34.0 | | | |
| Aryl ester (c) | | | 32.6 | | |
| Aryl ester (d) | | | | 37.4 | 33.7 |
| Dicyandiamide | | | | | |
| Curesol 2E4MZ | | 0.5 | 0.5 | 0.5 | 0.5 |
| Glass transition temp. | °C. | 138 | 139 | 155 | 151 |
| Copper foil-peeling strength | kg/cm | 1.58 | 1.43 | 1.58 | 1.88 |
| Boiling water absorption (48 hrs) | wt. % | 0.39 | 0.29 | 0.22 | 0.38 |
| Soldering heat resistance (normal state) | | 10 min or more | 10 min or more | 10 min or more | 10 min or more |
| Dielectric constant (at 1 GHz) | | 4.22 | 4.18 | 4.15 | 4.23 |
| Dielectric loss tangent (at 1 GHz) | | 0.0129 | 0.0122 | 0.0113 | 0.0131 |
| Flame-retardancy (UL 94) | | V-O | V-O | V-O | V-O |

EXAMPLES 32 to 35

The epoxy resin obtained in Synthesis Example 2 and diglycidyl ether of tetrabromobisphenol A (Sumi-®epoxy ESB-400T, a trade name of Sumitomo Chemical Co., Ltd., epoxy equivalent: 398 g/eq) (as required for adjusting the bromine content) were used as the epoxy resins, and blended with the compounds obtained in Synthesis Examples 9, 10, 11 and 12 and 2-ethyl-4-methylimidazole (cure accelerator) in the amounts shown in Table 5, and the resulting mixture was dissolved in a solvent to prepare a uniform resin varnish. Using the resin varnish obtained, there was obtained a copper-clad laminate having a thickness of 1 mm in the same manner as in Examples 23 to 31.

The copper-foil peeling strength, soldering heat resistance, boiling water absorption, glass transition temperature (Tg), dielectric constant at 1 GHz and dielectric loss tangent at 1 GHz of the laminate were measured in the same manner as in Examples 23 to 31. The measurement results are shown in Table 5.

TABLE 5

|  |  | Example No. | | | |
|---|---|---|---|---|---|
|  |  | 32 | 33 | 34 | 35 |
| Epoxy resin of Synthesis Ex. 2 | | 49.6 | 47 | 66.5 | 69.9 |
| Sumi-® epoxy ESB-500 | | | | | |
| Sumi-® epoxy ESB-400 | | 13.4 | 14.8 | 4.1 | 2.3 |
| Sumi-® epoxy ESCN-220 | | | | | |
| Aryl ester (a) | | 37 | | | |
| Aryl ester (b) | | | 38.2 | | |
| Aryl ester (c) | | | | 29.4 | |
| Aryl ester (d) | | | | | 27.8 |
| Dicyandiamide | | | | | |
| Curesol 2E4MZ | | 0.5 | 0.5 | 0.5 | 0.5 |
| Glass transition temp. | °C. | 136 | 132 | 142 | 141 |
| Copper fail-peeling strength | kg/cm | 1.78 | 1.75 | 1.87 | 1.95 |
| Boiling water absorption (48 hrs) | wt. % | 0.2 | 0.22 | 0.25 | 0.29 |
| Soldering heat resistance (normal state) | | 10 min or more | 10 min or more | 10 min or more | 10 min or more |
| Soldering heat resistance (after boiling) | | 10 min or more | 10 min or more | 10 min or more | 10 min or more |
| Dielectric constant (at 1 GHz) | | 3.95 | 3.99 | 4.07 | 4.11 |
| Dielectric loss tangent (at 1 GHz) | | 0.0121 | 0.0108 | 0.0125 | 0.0118 |

Comparative Example 5

A brominated epoxy resin (Sumi-®epoxy ESB-500, a trade name of Sumitomo Chemical Co., Ltd., epoxy equivalent: 472 g/eq) and cresol novolak type epoxy resin (Sumi-®epoxy ESCN-200, a trade name of Sumitomo Chemical Co., Ltd., epoxy equivalent: 215 g/eq) were used as the epoxy resins and blended with dicyandiamide and 2-ethyl-4-methylimidazole in the amounts shown in Table 6, and the resulting mixture was dissolved in a mixed solvent of methyl ethyl ketone and ethylene glycol monomethyl ether to prepare a uniform resin varnish. Using this resin varnish, a copper-clad laminate was prepared in the same manner as in Examples 23 to 35, and the physical properties of the laminate were measured in the same manner as in the Examples. The measurement results are shown in Table 6.

TABLE 6

|  |  | Comparative Example 5 |
|---|---|---|
| Sumi-® epoxy ESB-500 |  | 90 |
| Sumi-® epoxy ESCN-220 |  | 10 |
| Dicyandiamide |  | 2.49 |
| Curesol 2E4MZ |  | 0.1 |
| Glass transition temp. | °C. | 135 |
| Copper foil-peeling strength | kg/cm | 2.01 |
| Boiling water absorption (48 hrs) | % | 1.2 |
| Soldering heat resistance (normal state) |  | 10 min or more |
| Soldering heat resistance (after boiling) |  | 10 min or more |
| Dielectric constant (at 1 GHz) |  | 4.55 |
| Dielectric loss tangent (at 1 GHz) |  | 0.0205 |

The novel aryl ester compound of this invention can give, when used as a curing agent, a cured product having a lower dielectric constant and a lower dielectric loss tangent than conventional ones. An epoxy resin composition comprising the novel aryl ester compound and a copper-clad laminate obtained from the epoxy resin composition are low in dielectric constant and dielectric loss tangent as compared with conventional ones and are also excellent in adhesiveness. Therefore, the copper-clad laminate is suitable for multilayer printed wiring board for high speed operation, especially at high-frequency region.

What is claimed is:

1. An epoxy resin composition comprising as the essential components:

(A) an epoxy resin;

(B) an aryl ester compound composed of a polyhydric phenol in which at least one OH group has been esterified with an organic acid having an acetyl group or an aromatic ring free acyl group and having 1 to 20 carbon atoms, said polyhydric phenol being a condensation product of a phenolic compound represented by the general formula (4):

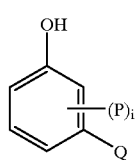

(4)

wherein each P represents independently a hydrogen atom, a halogen atom, an alkyl group having 1 to 10 carbon atoms, a cycloalkyl group having 5 to 10 carbon atoms, an aryl group having 6 to 20 carbon atoms or an aralkyl group having 7 to 20 carbon atoms and i represents an integer of 0 to 2, and Q represents a hydrogen atom or a hydroxyl group, with a carbonyl compound represented by the general formula (2):

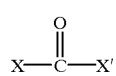

(2)

wherein each of X and X' represents independently a hydrogen atom, an alkyl group having 1 to 10 carbon atoms, a cycloalkyl group having 5 to 10 carbon atoms, an aryl group having 6 to 20 carbon atoms or an aralkyl group having 7 to 20 carbon atoms, provided that X and X' may form a ring together with the carbon atom to which X and X' are attached, said condensation being conducted in the presence of an acid catalyst; and (C) a cure accelerator, wherein in the aryl ester compound (B) the esterification percentage is at least 30 equivalent % relative to the total OH groups.

2. The epoxy resin composition according to claim 1, wherein the aryl ester compound (B) is an aryl ester compound represented by the general formula (3):

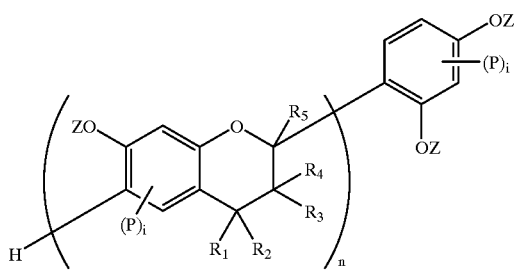

(3)

wherein n represents the average number of the repeated units and is a value of 1 to 20; each P represents independently a hydrogen atom, a halogen atom, an alkyl group having 1 to 10 carbon atoms, a cycloalkyl group having 5 to 10 carbon atoms, an aryl group having 6 to 20 carbon atoms or an aralkyl group having 7 to 20 atoms; i represents an integer of 0 to 2; each of $R_1$, $R_2$, $R_3$, $R_4$ and $R_5$ represents independently a hydrogen atom, an alkyl group having 1 to 10 carbon atoms, a cycloalkyl group having 5 to 10 carbon atoms, an aryl group having 6 to 20 carbon atoms or an aralkyl group having 7 to 20 carbon atoms; provided that $R_1$ and $R_2$ may form a ring together with the carbon atom to which $R_1$ and $R_2$ are attached or $R_4$ and $R_5$ may form a ring together with the carbon atoms to which $R_4$ and $R_5$ are attached; each Z represents independently a hydrogen atom or an acyl group having 1 to 20 carbon atoms, provided that the case where all Z groups are hydrogen atoms is excluded.

3. The epoxy resin composition according to claim 1, wherein the aryl ester compound (B) is composed of a polyhydric phenol in which at least one OH group has been esterified with an organic acid or its derivatives having 1 to 20 carbon atoms, said polyhydric phenol being the condensation product of a substituted or unsubstituted resorcinol represented by the general formula (1):

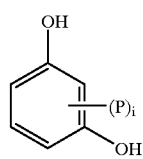

(1)

wherein each p represents independently a hydrogen atom, a halogen atom, an alkyl group having 1 to 10 carbon atoms, a cycloalkyl group having 5 to 10 carbon atoms, an aryl group having 6 to 20 carbon atoms or an aralkyl group having 7 to 20 carbon atoms and i represents an integer of 0 to 2, with a carbonyl compound represented by the general formula (2):

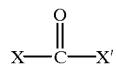

wherein each of X and X' represents independently a hydrogen atom, an alkyl group having 1 to 10 carbon atoms, a cycloalkyl group having 5 to 10 carbon atoms, an aryl group having 6 to 20 carbon atoms or an aralkyl group having 7 to 20 carbon atoms, provided that X and X' may form a ring together with the carbon atom to which X and X' are attached, said condensation being conducted in the presence of an acid catalyst.

4. An epoxy resin composition according to claim 1, wherein said organic acid has an acetyl group.

5. An epoxy resin composition comprising as the essential components:

(A) an epoxy resin;
(B) an aryl ester compound composed of a polyhydric phenol in which at least one OH group has been esterified with an organic acid or its derivatives having 1 to 20 carbon atoms, said polyhydric phenol being a condensation product of a phenolic compound represented by the general formula (4):

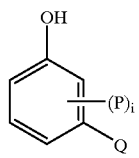

wherein each P represents independently a hydrogen atom, a halogen atom, an alkyl group having 1 to 10 carbon atoms, a cycloalkyl group having 5 to carbon atoms, an aryl group having 6 to 20 carbon atoms or an aralkyl group having 7 to 20 carbon atoms and i represents an integer of 0 to 2, and Q represents a hydrogen atom or a hydroxyl group, with a carbonyl compound represented by the general formula (2):

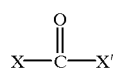

wherein each of X and X' represents independently a hydrogen atom, an alkyl group having 1 to 10 carbon atoms, a cycloalkyl group having 5 to 10 carbon atoms, an aryl group having 6 to 20 carbon atoms or an aralkyl group having 7 to 20 carbon atoms, provided that X and X' may form a ring together with the carbon atom to which X and X' are attached, said condensation being conducted in the presence of an acid catalyst wherein said aryl ester compound is represented by the general formula (5):

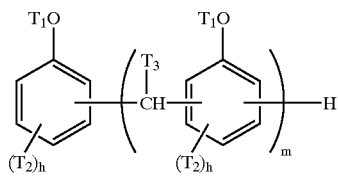

wherein m represents the average number of the repeated units and is a value of 1 to 10; each $T_1$ represents independently a hydrogen atom or an aromatic ring-free acyl group having 1 to 20 carbon atoms, provided that the case where all $T_1$ groups are hydrogen atoms is excluded; each $T_2$ represents independently a hydrogen atom, an alkyl group having 1 to 10 carbon atoms or a cycloalkyl group having 5 to 7 carbon atoms; h represents an integer of 1 to 3, provided that when h is 2 or 3, each $T_2$ may be the same as or different from one another in one and the same ring; each $T_3$ represents independently a hydrogen atom, an alkyl group having 1 to 10 carbon atoms, an aryl group having 6 to 20 carbon atoms or an aralkyl group having 7 to 20 carbons; and (C) a cure accelerator.

6. The epoxy resin composition according to claim 5, wherein the epoxy resin (A) is a compound represented by the general formula (6):

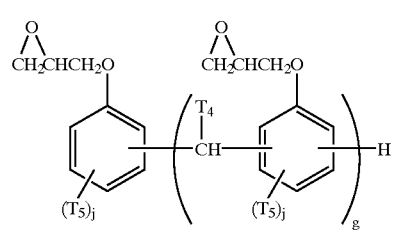

wherein g represents the average number of the repeated units and is a value of 1 to 10; each $T_4$ represents independently a hydrogen atom or an alkyl group having 1 to 10 carbon atoms; each $T_5$ represents independently an alkyl group having 1 to 10 carbon atoms or a cycloalkyl group having 5 to 10 carbon atoms, provided that at least one $T_5$ group is an alkyl group having 4 to 10 carbon atoms or a cycloalkyl group 5 to 7 carbon atoms in one and the same ring; and j represents an integer of 1 to 3, provided that when j is 2 to 3, each $T_5$ may be the same or different from one another in one and the same ring.

7. The epoxy resin composition according to claim 5, wherein the epoxy resin (A) is an epoxy resin obtained by reacting an epoxy resin with a halogen-containing bisphenol compound represented by the general formula (7):

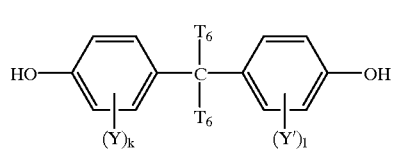

wherein each $T_6$ represents a hydrogen atom or a methyl group and two $T_6$ groups may be the same as or different from each other; Y and Y', which may be the same as or different from each other, represent halogen atoms; and each of k and l represents an integer of 1 to 4.

8. The epoxy resin composition according to claim 5, wherein the epoxy resin (A) is an epoxy resin obtained by reacting an epoxy resin represented by the general formula (6):

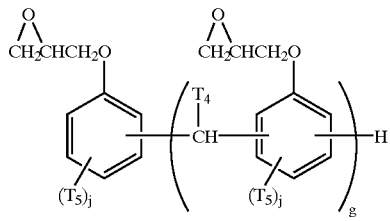

(6)

wherein g represents the average number of the repeated units and is a value of 1 to 10; each $T_4$ represents independently a hydrogen atom or an alkyl group having 1 to 10 carbon atoms; each $T_5$ represents independently an alkyl group having 1 to 10 carbon atoms or a cycloalkyl group having 5 to 10 carbon atoms, provided that at least one $T_5$ group is an alkyl group having 4 to 10 carbon atoms or a cycloalkyl group having 5 to 7 carbon atoms in one and the same ring; and j represents an integer of 1 to 3, provided that when j is 2 or 3, each $T_5$ may be the same as or different from one another in one and the same ring, with a halogen-containing bisphenol compound represented by the general formula (7):

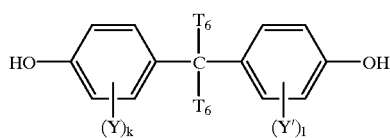

(7)

wherein each $T_6$ represents a hydrogen atom or a methyl group and two $T_6$ groups may be the same as or different from each other, Y and Y', which may be the same as or different from each other, represent halogen atoms; and each of k and l represents independently an integer of 1 to 4.

9. The epoxy resin composition according to claim 5, wherein in the aryl ester compound (B) the esterification percentage is at least 30 equivalent percent relative to the total OH groups.

10. The epoxy resin composition according to claim 5, wherein the ratio of the number of mols of the acyl groups in the aryl ester compound to the number of mols of the epoxy group in the epoxy resin is 0.3:1 to 1.5:1.

11. An epoxy resin composition comprising as the essential components:

(A) an epoxy resin which is obtained by reacting an epoxy resin with a halogen-containing bisphenol compound that is represented by the general formula (7):

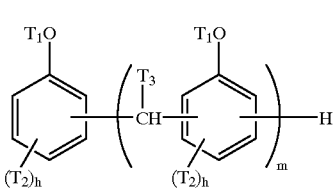

(5)

wherein each $T_6$ represents a hydrogen atom or a methyl group and two $T_6$ groups may be the same as or different from each other; Y and Y', which may be the same as or different from each other, represent halogen atoms; and each of k and l represents independently an integer of 1 to 4, (B) an aryl ester represented by the general formula (3):

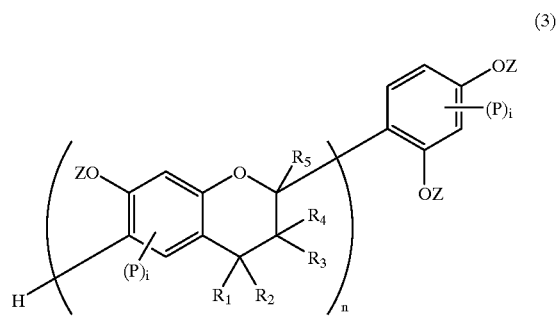

(3)

wherein n represents the average number of the repeated units and is a value of 1 to 20; each P represents independently a hydrogen atom, a halogen atom, an alkyl group having 1 to 10 carbon atoms, a cycloalkyl group having 5 to 10 carbon atoms, an aryl group having 6–20 carbon atoms or an aralkyl group having 7 to 20 atoms; i represents an integer of 0 to 2; each of $R_1$, $R_2$, $R_3$, $R_4$, and $R_5$ represents independently a hydrogen atom, an alkyl group having 1 to 10 carbon atoms, a cycloalkyl group having 5 to 10 carbon atoms, an aryl group having 6 to 20 carbon atoms or an aralkyl group having 7 to 20 carbon atoms, provided that $R_1$ to $R_2$ may form a ring together with the carbon atom to which $R_1$ and $R_2$ are attached or $R_4$ and $R_5$ may form a ring together with the carbon atoms to which $R_4$ and $R_5$ are attached; each Z represents independently a hydrogen atom and an acyl group having 1 to 20 carbon atoms, provided that the case where all Z groups are hydrogen atoms is excluded; and (C) a cure accelerator, wherein the aryl ester compound (B) the esterification percentage is at least 30 equivalent percent relative to the total OH groups.

12. The epoxy resin composition according to any one of claims 1, 3 or 2, wherein the epoxy resin (A) is a compound represented by the general formula (6):

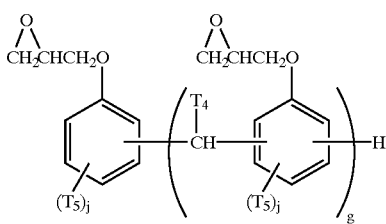

(6)

wherein g represents the average number of the repeated units and is a value of 1 to 10; each $T_4$ represents independently a hydrogen atom or an alkyl group having 1 to 10 carbon atoms; each $T_5$ represents independently an alkyl group having 1 to 10 carbon atoms or a cycloalkyl group having 5 to 10 carbon atoms, provided that at least one $T_5$ group is an alkyl group having 4 to 10 carbon atoms or a cycloalkyl group having 5 to 7 carbon atoms in one and the same ring; and j represents an integer of 1 to 3, provided that when j is 2 or 3, $T_5$'s may be the same as or different from one another in one and the same ring.

13. The epoxy resin composition according to any one of claims 1, 3 or 2, wherein the epoxy resin (A) is an epoxy resin obtained by reacting an epoxy resin represented by the general formula (6):

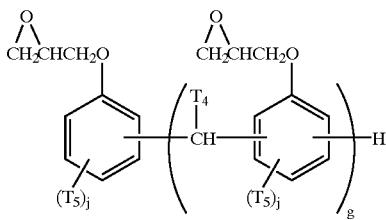

(6)

wherein g represents the average number of the repeated units and is a value of 1 to 10; each $T_4$ represents independently a hydrogen atom or an alkyl group having 1 to 10 carbon atoms; each $T_5$ represents independently an alkyl group having 1 to 10 carbon atoms or a cyclo alkyl group having 5 to 10 carbon atoms, provided that at least one $T_5$ group is an alkyl group having 4 to 10 carbon atoms or a cyclo alkyl group having 5 to 7 carbon atoms in one and the same ring; and j represents an integer of 1 to 3, provided that when j is 2 or 3, the $T_5$ groups may be the same as or different from one another in one and the same ring, with a halogen-containing bisphenol compound represented by the general formula (7):

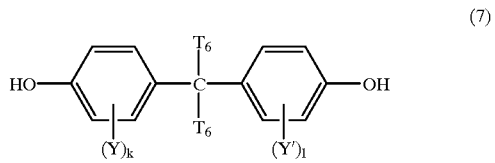

(7)

wherein each $T_6$ represents a hydrogen atom or a methyl group and two $T_6$ groups may be the same as or different from each other; Y and Y', which may be the same as or different from one another, represent halogen atoms; and each of k and l represents independently an integer of 1 to 4.

14. The epoxy resin composition according to any one of claims 1, 3, 2, wherein the aryl ester compound (B) the esterfication percentage is at least 50 equivalent percent relative to the total OH groups.

15. The epoxy resin composition according to any one of claims 1, 3, 2, wherein the ratio of the number of moles of the acyl groups in the aryl ester compound to the number of moles of the epoxy groups in the epoxy resin is 0.3:1 to 1.5:1.

* * * * *